US00PP36856P2

(12) United States Plant Patent
Bak

(10) Patent No.: US PP36,856 P2
(45) Date of Patent: Jul. 22, 2025

(54) ***ALPINIA* PLANT NAMED 'Crispy'**

(50) Latin Name: *Alpinia rugosa*
Varietal Denomination: Crispy

(71) Applicant: Corn Bak BV, Assendelft (NL)

(72) Inventor: Elly Bak, Assendelft (NL)

(73) Assignee: Corn Bak B.V. (NL)

( * ) Notice: Subject to any disclaimer, the term of this patent is extended or adjusted under 35 U.S.C. 154(b) by 0 days.

(21) Appl. No.: 18/911,551

(22) Filed: Oct. 10, 2024

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP33,884 P2 * 1/2022 Liu ..... Plt./313

* cited by examiner

*Primary Examiner* — Karen M Redden
(74) *Attorney, Agent, or Firm* — Cassandra Bright

(57) ABSTRACT

A new and distinct cultivar of *Alpinia* plant named 'CRISPY' is disclosed, characterized by a solid growth habit which is firm and does not lodge over. Plants are strong, making them suitable for long-lasting ornamental use. Leafy blades are uniquely wavy. The new variety is an *Alpinia* typically produced as an ornamental plant.

1 Drawing Sheet

Latin name of the genus and species: *Alpinia rugosa.*
Variety denomination: 'CRISPY'.

BACKGROUND OF THE INVENTION

The present invention relates to a new and distinct cultivar of *Alpinia* plant, botanically known as *Alpinia*, of the family Zingiberaceae, and hereafter referred to as 'CRISPY'.

The new *Alpinia* 'Crispy' originated as a seedling selection resulting from the selfing of the species *Alpinia rugosa* by the inventor in 2020. The parent is the unnamed and unpatented plant of *Alpinia rugosa*. The new *Alpinia* was discovered and selected by the inventor in 2020 as a single plant in a controlled environment commercial greenhouse in Assendelft, the Netherlands.

Asexual reproduction of the new cultivar 'CRISPY' was first performed by off-shoots beginning in 2020, and subsequently by tissue culture in 2021 in Assendelft, the Netherlands. The new cultivar reproduces true to type by these asexual methods.

*Alpinia* is a member of the Zingiberaceae family. The Zingiberaceae, or ginger family consists of 52 genera and more than 1300 species that are distributed throughout tropical Africa, Asia, and the Americas. *Alpinia* can be easily distinguished from other genera by its large herbs, terminal panicle, raceme, or spike, small or absent lateral staminodes, and often showy labellum (Larsen, 1998; Wu & Larsen, 2000). The species *Alpinia rugosa* is only known from Hainan, China and is distinguished by its entirely wrinkled leaves, orange labellum, subulate lateral staminodes, and gamboge or deep yellow mature fruits. The species *Alpinia rugosa* occurs in wet, shaded habitats in valley forest. Reference: Pu Zou, Yu-Shi Ye, Sen-Jen Chen, Zhong-Yi Chen, and Jing-Ping Liao Source: Novon: A Journal for Botanical Nomenclature, 22(1):128-130. 2012. Published By: Missouri Botanical Garden (2012).

SUMMARY OF THE INVENTION

The following traits have been repeatedly observed and are determined to be the unique characteristics of 'CRISPY', which in combination distinguish 'CRISPY' as a new and distinct *Alpinia* cultivar:

1. Solid growth habit; upright and not lodging over.
2. Wavy leaf blade.
3. Suitability for ornamental use.
4. Long-lasting ornamental plant.
5. Compact plant suitable for production in 14 cm pots.
6. Short pseudostems, at least 20% shorter than the species.
6. Upright pseudostems with a more acute angle than the species.

PARENT COMPARISON

Plants of the new cultivar *Alpinia rugosa* 'CRISPY' are similar to the parent in most horticultural characteristics. The new cultivar exhibits the following differences from the parent plant:

1. *Alpinia* 'Crispy' has a more compact growth habit than the parent plant.
2. The pseudostems of *Alpinia* 'Crispy' are shorter than pseudostems of the parent plant. Pseudostems of the new variety are at least 20% shorter than pseudostems of the parent.
3. Plants of the of new variety are upright with pseudostems occurring at acute angles from the center; plant habit of the parent is semi-spreading with broader angles of the pseudostems from the center of the plant.

COMMERCIAL COMPARISONS

*Alpinia* 'Crispy' can be compared to the variety *Alpinia* 'LY1' U.S. Plant Pat. No. 33,884. Both varieties are in the

*Alpinia* genus and useful for commercial ornamental purposes. 'Crispy' differs from 'LY1' in the following:

1. 'Crispy' is a small plant of about 25 cm high at maturity used as an ornamental indoor foliage plant. 'LY1' is a large plant useful for cut flowers and landscape purposes, reaching 250 to 350 cm in height.
2. 'Crispy' has not been observed to flower to date; 'LY1' flowers regularly and for up to 8 months at a time.

BRIEF DESCRIPTION OF THE PHOTOGRAPH

The accompanying photograph illustrates the overall appearance of the new *Alpinia* cultivar 'CRISPY' showing the colors as true as is reasonably possible with colored reproductions of this type. Colors in the photograph may differ slightly from the color values cited in the detailed botanical description which accurately describes the color of 'CRISPY'. The accompanying figure shows a side perspective view of a typical potted flowering plant of 'CRISPY' at about 16 months of age from potting.

DETAILED BOTANICAL DESCRIPTION

'CRISPY' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photograph, together with the following observations, measurements and values describe the new *Alpinia* 'CRISPY' as grown in a greenhouse in Assendelft, The Netherlands, under conditions which closely approximate those generally used in commercial practice. Plants of 'CRISPY' were grown in a greenhouse with day temperatures ranging from 20° C. to 28° C. and night temperatures ranging from 18° C. to 23° C. No artificial lighting or photoperiodic treatments were conducted, but plants of 'CRISPY' are forced into flowering. The following fertilizer is added when growing plants of 'CRISPY': 1 part nitrogen, 0.6 parts phosphor, 2 parts Kalium and 0.1 parts magnesium.

Color references are made to The Royal Horticultural Society Colour Chart (R.H.S.), 2001 edition, except where general colors of ordinary significance are used. Color values were taken under daylight conditions in a greenhouse in Assendelft, The Netherlands.

Botanical classification: *Alpinia* 'CRISPY'.

PROPAGATION

Propagation method: Tissue culture.

PLANT

General appearance and form:

*Shape*.—Upright and outward, forming a wide V-shape.

*Height*.—About 25 cm.

*Width*.—About 40 cm.

Growth habit: Herbaceous ornamental with pseudostems.

Plant vigor: Good.

Growth rate: Rapid.

Cold tolerance: Frost tender. Temperatures below 0° C. may damage plants.

Pseudostems:

*Average length*.—25-40 cm.

*Average width*.—0.5 cm (at the middle part).

*Average quantity*.—14.

*Ligule*.—Length: approximately 1 cm. Texture: coriaceous.

FOLIAGE

Leaf:

*Quantity*.—About 8 per pseudostem.

*Average length*.—25 cm.

*Average width*.—5 to 5.5 cm.

*Shape*.—Oblong.

*Aspect*.—Strongly wavy.

*Apex*.—Cirrose.

*Base*.—Clasping.

*Margin*.—Entire.

*Texture*.—Upper surface glabrous. Lower surface densely pubescent.

*Color*.—Immature, Upper Side: RHS Yellow-Green 144A. Immature, Under Side: RHS Yellow-Green 146B. Mature, Upper side: RHS Green 137A. Mature Under side: RHS Green 137B.

*Venation*.—Type: Linear. Color upper side: RHS Green 136C. Color under side: RHS Green 137B.

FLOWERS

Flowering and fruiting not observed to date.

OTHER CHARACTERISTICS

Seeds: Not observed to date.

Fruit: Not observed to date.

Disease/pest resistance: No resistance nor susceptibility to normal diseases and pests of *Alpinia* have been observed.

What is claimed is:

1. A new and distinct cultivar of *Alpinia* plant named 'CRISPY' as herein illustrated and described.

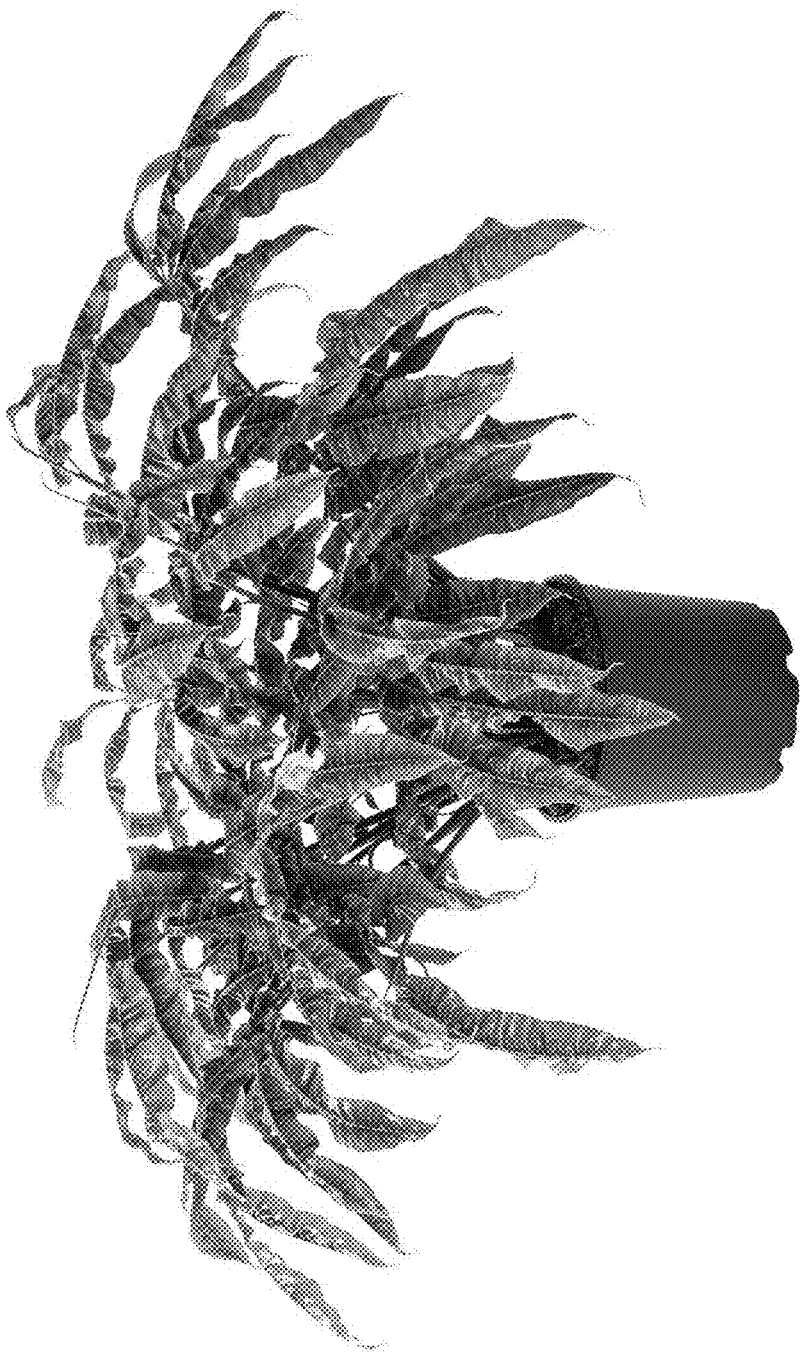

* * * * *